US011420037B2

(12) United States Patent
Crnkovich et al.

(10) Patent No.: US 11,420,037 B2
(45) Date of Patent: Aug. 23, 2022

(54) INFUSION METHODS FOR EXTRACOPOREAL SYSTEMS

(71) Applicants: Fresenius Medical Care Holdings, Inc., Waltham, MA (US); Fresenius Medical Care Deutschland GmbH, Bad Homburg (DE)

(72) Inventors: Martin Joseph Crnkovich, Walnut Creek, CA (US); David Yuds, Antioch (CA); Christian Schlaeper, Waltham, MA (US)

(73) Assignees: Fresenius Medical Care Holdings, Inc., Waltham, MA (US); Fresenius Medical Care Deutschland GmbH, Bad Homburg (DE)

( * ) Notice: Subject to any disclaimer, the term of this patent is extended or adjusted under 35 U.S.C. 154(b) by 417 days.

(21) Appl. No.: 15/669,287

(22) Filed: Aug. 4, 2017

(65) Prior Publication Data

US 2019/0038890 A1    Feb. 7, 2019

(51) Int. Cl.
| | | |
|---|---|---|
| A61M 39/28 | (2006.01) | |
| A61M 1/36 | (2006.01) | |
| A61M 1/26 | (2006.01) | |

(52) U.S. Cl.
CPC ............ *A61M 39/28* (2013.01); *A61M 1/267* (2014.02); *A61M 1/3646* (2014.02);
(Continued)

(58) Field of Classification Search
None
See application file for complete search history.

(56) References Cited

U.S. PATENT DOCUMENTS 5,591,344 A    1/1997  Kenley et al.
5,690,831 A *  11/1997 Kenley .................... A61L 2/04
                                            210/646
(Continued)

FOREIGN PATENT DOCUMENTS

| CA | 2181024 | 1/1997 |
| EP | 0754468 | 1/1997 |
(Continued)

OTHER PUBLICATIONS

"5008 Hemodialysis system: Operation Instructions," Fresenius Medical Care, Edition 10/08.13, Part No. M518941, 382 pages.
(Continued)

*Primary Examiner* — Jonathan M Peo
(74) *Attorney, Agent, or Firm* — Fish & Richardson P.C.

(57) ABSTRACT

A method of operating an extracorporeal blood treatment system to infuse blood into a patient at an end of an extracorporeal blood treatment includes clamping an access line of an arterial line set. The method further includes, after clamping the access line, initiating an operation to generate negative pressure in the arterial line set. The method further includes, after generating the negative pressure in the arterial line set, unclamping the access line to draw fluid in the access line further into the arterial line set in a direction away from an end of the access line that is connectable to an arterial access of the patient. The method further includes initiating an operation of a fluid pump engaged with the arterial line set such that the fluid in the arterial line set is infused into the patient through a venous line set.

25 Claims, 6 Drawing Sheets

(52) U.S. Cl.
CPC ........ *A61M 1/3653* (2013.01); *A61M 1/3661* (2014.02); *A61M 2205/3306* (2013.01); *A61M 2205/3331* (2013.01); *A61M 2205/3334* (2013.01); *A61M 2205/505* (2013.01)

(56) References Cited

U.S. PATENT DOCUMENTS

| | | |
|---|---|---|
| 5,772,624 A | 6/1998 | Utterberg et al. |
| 5,895,368 A | 4/1999 | Utterberg |
| 6,165,149 A | 12/2000 | Utterberg et al. |
| 6,290,665 B1 | 9/2001 | Utterberg |
| 6,387,069 B1 | 5/2002 | Utterberg |
| 6,620,119 B1 | 9/2003 | Utterberg et al. |
| 6,649,063 B2 | 11/2003 | Brugger et al. |
| 6,666,839 B2 | 12/2003 | Utterberg et al. |
| 7,166,084 B2 | 1/2007 | Utterberg |
| 7,214,312 B2 | 5/2007 | Brugger et al. |
| 7,226,538 B2 | 6/2007 | Brugger et al. |
| 7,387,734 B2 | 6/2008 | Felding |
| 7,419,597 B2 | 9/2008 | Brugger et al. |
| 7,588,684 B2 | 9/2009 | Brugger et al. |
| 7,780,848 B2 | 8/2010 | Kim et al. |
| 7,790,043 B2 | 9/2010 | Brugger et al. |
| 8,409,441 B2 | 4/2013 | Wilt |
| 8,491,518 B2 | 7/2013 | Schnell et al. |
| 8,608,680 B2 | 12/2013 | Hasegawa |
| 8,721,884 B2 | 5/2014 | Wilt et al. |
| 9,480,784 B2 | 11/2016 | Kelly et al. |
| 9,555,179 B2 | 1/2017 | Wilt et al. |
| 2002/0151834 A1 | 10/2002 | Utterberg |
| 2003/0100858 A1 | 5/2003 | Utterberg et al. |
| 2005/0131331 A1* | 6/2005 | Kelly .................. A61M 1/34 604/4.01 |
| 2007/0106196 A1 | 5/2007 | Utterberg |
| 2009/0124963 A1 | 5/2009 | Hogard et al. |
| 2009/0312686 A1 | 12/2009 | Sakamoto et al. |
| 2013/0310726 A1* | 11/2013 | Miller ................ A61M 1/288 604/5.04 |
| 2014/0158589 A1 | 6/2014 | Furuhashi |
| 2016/0030657 A1* | 2/2016 | Kelly ................. A61M 1/1696 210/646 |
| 2016/0074571 A1* | 3/2016 | Kopperschmidt .. A61M 1/3656 604/5.04 |

FOREIGN PATENT DOCUMENTS

| | | |
|---|---|---|
| EP | 2752210 | 7/2014 |
| JP | H09122230 | 5/1997 |
| JP | 2001-252352 | 9/2001 |
| JP | 2006-020967 | 1/2006 |

OTHER PUBLICATIONS

"Set-Up and Prime (con't)," Phoenix Training Manual, Gambro Lundia AB 306050288, Rev. G., 2007, p. 6.

"Section 5—Dialysis Operation: 5.10-5.10.1," Phoenix Operator Manual, Rev. A., p. 52-53.

International Search Report and Written Opinion in Application No. PCT/US2018/042852, dated Nov. 12, 2018, 11 pages.

International Preliminary Report on Patentability in Application No. PCT/US2018/042852, dated Feb. 4, 2020, 7 pages.

\* cited by examiner

INFUSION METHODS FOR EXTRACOPOREAL SYSTEMS

TECHNICAL FIELD

This specification relates to infusion methods for extracorporeal systems.

BACKGROUND

During an extracorporeal fluid treatment, blood is circulated through an extracorporeal fluid circuit to filter waste from the blood. A pump can be operated to generate a flow of blood drawn from the patient through an arterial line set, through a filter, then back into the patient through a venous line set. The venous line set and the arterial line set can be connected to the patient to enable the blood to be drawn from the patient and to be returned to the patient after the blood flows through the filter. At the end of the extracorporeal treatment, some residual blood that has not been returned to the patient during the extracorporeal treatment may remain with the arterial line set and the venous line set. In some cases, a syringe can be connected to the arterial line set or the venous line set and can be manually actuated to exert a positive pressure on the residual blood within the arterial line set and the venous line set to return the blood to the patient.

SUMMARY

In one aspect, a method of operating an extracorporeal blood treatment system to infuse blood into a patient at an end of an extracorporeal blood treatment includes clamping an access line of an arterial line set. The arterial line set includes an arterial line connectable to the access line, and the access line is connectable to an arterial access of the patient. The method further includes, after clamping the access line, initiating an operation to generate negative pressure in the arterial line set. The method further includes, after generating the negative pressure in the arterial line set, unclamping the access line to draw fluid in the access line further into the arterial line set in a direction away from an end of the access line that is connectable to the arterial access of the patient. The method further includes initiating an operation of a fluid pump engaged with the arterial line set such that the fluid in the arterial line set is infused into the patient through a venous line set.

In another aspect, an extracorporeal blood treatment system includes a fluid pump configured to engage an arterial line set to convey fluid from a patient through the arterial line set, through a dialyzer, through a venous line set, and back to the patient during an extracorporeal blood treatment. The extracorporeal blood treatment system further includes a controller configured to operate the fluid pump to generate negative pressure in the arterial line set to draw fluid toward the fluid pump engaged to the arterial line set while an access line of the arterial line set is clamped, and infuse the fluid in the arterial line set into the patient through the venous line set while the access line of the arterial line set is unclamped.

In some implementations, the method further includes, after the end of the extracorporeal blood treatment and before clamping the access line, initiating an operation to deactivate an ultrafiltration pump and to deactivate the fluid pump.

In some implementations, the method further includes clamping a port of the arterial line set, the port being connectable to a fluid source. In some cases, the operation to generate the negative pressure is initiated while the port and the access line of the arterial line set are clamped.

In some implementations, the method further includes disconnecting a port of the arterial line set from a fluid source, and connecting the access line to the fluid source. In some cases, the method further includes clamping a fluid line connecting the fluid source to the port of the arterial line set before disconnecting the port.

In some implementations, the method further includes removing an arterial needle, connected to the access line, from the arterial access. The operation to generate the negative pressure can be initiated while the arterial needle is removed. In some cases, the method further includes disconnecting the arterial needle from the access line after unclamping the access line.

In some implementations, the operation to generate the negative pressure in the arterial line set is initiated to draw the fluid in the arterial line set into a drip chamber of the arterial line set.

In some implementations, the method further includes connecting the access line to a fluid source. The access line can be unclamped before the fluid pump is operated to infuse the fluid and after the access line is connected to the fluid source, thereby causing fluid from the fluid source to be drawn toward the fluid pump by the negative pressure.

In some implementations, the operation of the fluid pump is initiated such that the fluid is drawn from the arterial line set, through a dialyzer, through the venous line set, and into the patient.

In some implementations, the fluid in the arterial line set includes a first fluid. The operation of the fluid pump can be initiated while the access line is connected to a fluid source such that a second fluid is pumped from the fluid source through the arterial line set and the venous line set to convey the first fluid through the arterial line set and the venous line set into the patient. In some cases, the first fluid includes blood. In some cases, the second fluid includes saline.

In some implementations, the fluid pump is driven in a direction in which the fluid pump is driven to perform the extracorporeal blood treatment on the patient.

In some implementations, initiating the operation to generate the negative pressure includes activating the fluid pump.

In some implementations, the extracorporeal blood treatment system further includes a pressure sensor to detect a value of pressure within the arterial line set. The controller can be configured to deactivate the fluid pump when the detected value of pressure exceeds a predefined value.

In some implementations, the extracorporeal blood treatment system further includes an optical sensor to detect flow of blood through the venous line set. The controller can be configured to deactivate the fluid pump when the optical sensor detects an absence of the flow of blood through the venous line set.

In some implementations, the controller is configured to operate the fluid pump for a duration of time between 5 and 15 seconds, while the access line of the arterial line set is clamped, to generate the negative pressure.

In some implementations, the extracorporeal blood treatment system further includes an ultrafiltration pump. The controller can be configured to deactivate the ultrafiltration pump and the fluid pump at an end of the extracorporeal blood treatment.

Advantages of the foregoing may include, but are not limited to, those described below and herein elsewhere. For example, less blood that is drawn from the patient is discarded as waste when the arterial line set and the venous line set are discarded. A greater amount of the residual blood in the arterial line set and the venous line set present at the end of an extracorporeal treatment can be returned to the patient during a blood reinfusion process described herein. The patient can thus experience less blood loss due to the extracorporeal treatment, and operators, e.g., clinicians and nurses, can be at a lower risk of being exposed to hazardous medical fluid waste.

In some examples, the blood reinfusion process can be accurately and precisely controlled through use of the fluid pump during the blood reinfusion process to return the blood to the patient. Rather than requiring manual operation of a pump mechanism, such as a syringe, a human operator initiates operation of the fluid pump whose pressure and flow rate can be accurately and precisely controlled. The blood reinfusion process can, for example, be an automated process in which the fluid pump controls the infusion of the residual blood based on detected pressure or fluid flow, thereby reducing the likelihood of human errors that could occur during a manual blood reinfusion process. In addition, this automated process can reduce the risk that high pressures are placed on the vascular system of the patient due to manual operation of a pump mechanism.

Furthermore, because the fluid pump is used to return the blood to the patient, the arterial line set and the venous line set do not need to be connected to a pumping mechanism external to the systems used to perform the extracorporeal blood treatment. This simplifies and reduces manual operations, such as disconnecting and connecting the arterial line set or the venous line set, performed by the human operator during the blood reinfusion process. In addition, the blood reinfusion process need not require special equipment but, rather, relies on a fluid pump, a fluid source, clamps, and other devices that are typically already used during the extracorporeal treatment.

In cases in which a pumping mechanism is connected to the arterial line set to return the blood to the patient, an arterial needle assembly connecting the arterial line set to the patient may need to be disconnected from the arterial line set to enable the pumping mechanism to be connected to the arterial line set. This can render the blood within the arterial needle assembly inaccessible during a blood reinfusion process. In contrast, the fluid pump can be used to first draw the blood from the arterial needle assembly into the arterial line set before the arterial needle assembly is disconnected from the arterial needle assembly, thus allowing a greater portion of the blood to be returned to the patient.

In further examples, because the blood is returned to the patient by drawing a liquid fluid through the arterial line set and the venous line set, air does not need to be drawn into the arterial line set and the venous line set. This can thus reduce the risk that air is pumped into the circulatory system of the patient.

The details of one or more implementations of the subject matter described in this specification are set forth in the accompanying drawings and the description below. Other potential features, aspects, and advantages will become apparent from the description, the drawings, and the claims.

DETAILED DESCRIPTION

Figure 1:
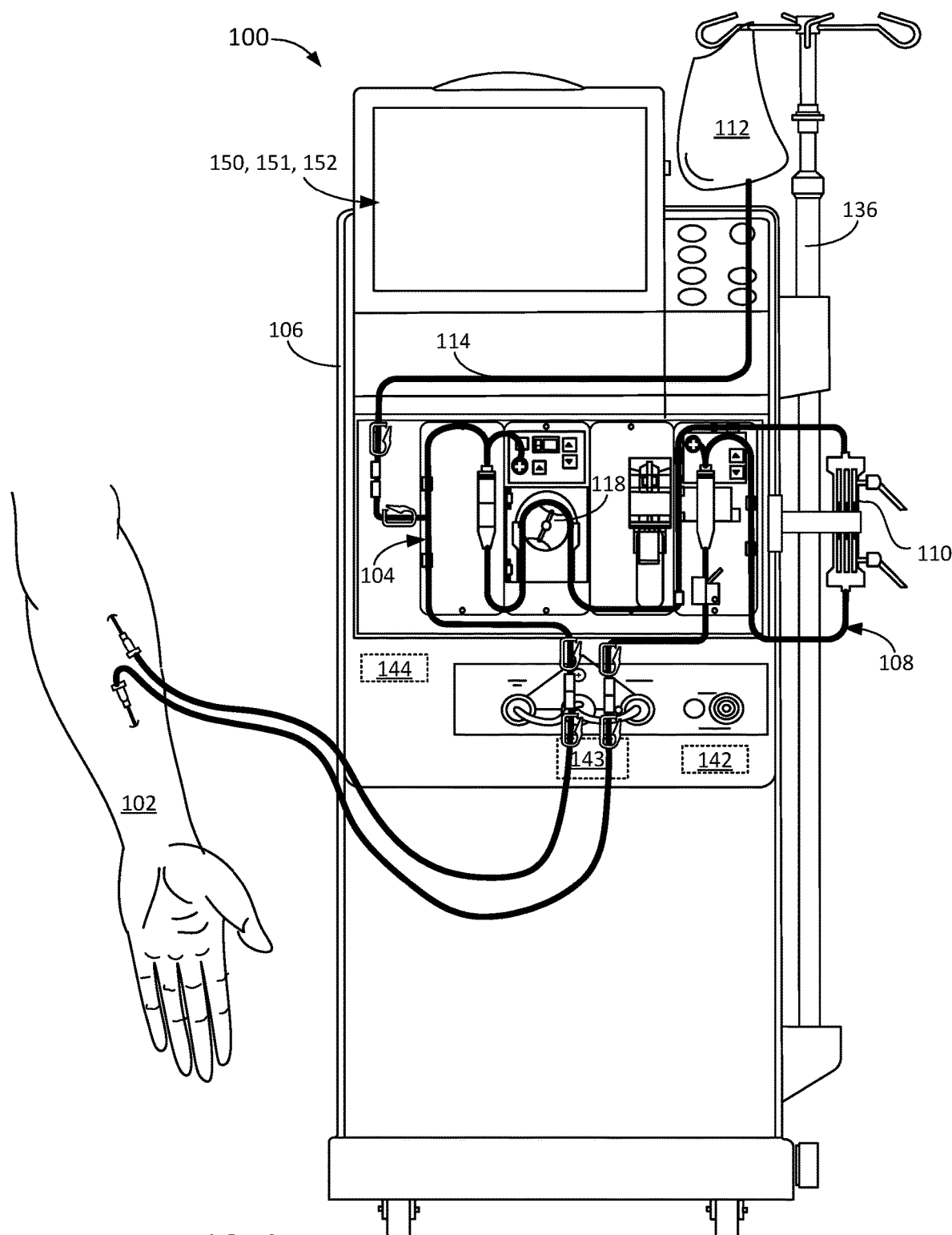
FIG. 1 illustrates an extracorporeal medical fluid treatment system including an extracorporeal blood circuit connected to a patient undergoing an extracorporeal treatment.

Referring to FIG. 1, during an extracorporeal treatment (e.g., a dialysis treatment) of a patient 102, an extracorporeal medical fluid treatment system 100 is operated to filter blood drawn from the patient 102. Blood from the patient 102 is drawn from the circulatory system of the patient 102 and circulated through the extracorporeal system 100. As described herein, after the extracorporeal treatment is complete, a negative pressure is generated within an arterial line set 104 to return blood to the patient 102 during a blood reinfusion process.

The extracorporeal system 100 includes an extracorporeal blood treatment machine 106, the arterial line set 104, a venous line set 108, a dialyzer 110, a fluid source 112, and a fluid line 114. The machine 106 is a dialysis machine, and the extracorporeal treatment performed by the machine 106 is a dialysis treatment. The machine 106 is a reusable apparatus operated to draw blood from the patient 102 through the arterial line set 104, through the dialyzer 110, through the venous line set 108, and back to the patient 102. The machine 106 can be used for multiple extracorporeal treatments. The machine 106 includes a blood pump 118 operable to draw blood from the patient 102.

The arterial line set 104, the venous line set 108, and the dialyzer 110 are disposable portions of the extracorporeal system 100. Because these disposable portions of the extracorporeal system 100 come into contact with the blood, these portions can be single-use components that are discarded after a single extracorporeal treatment. After the end of the extracorporeal treatment, the arterial line set 104, the venous line set 108, and the dialyzer 110 may contain residual blood drawn from the patient 102 during the extracorporeal treatment. This blood, through the blood reinfusion process described herein, can be returned to the patient 102 to reduce patient blood loss.

Figure 2:
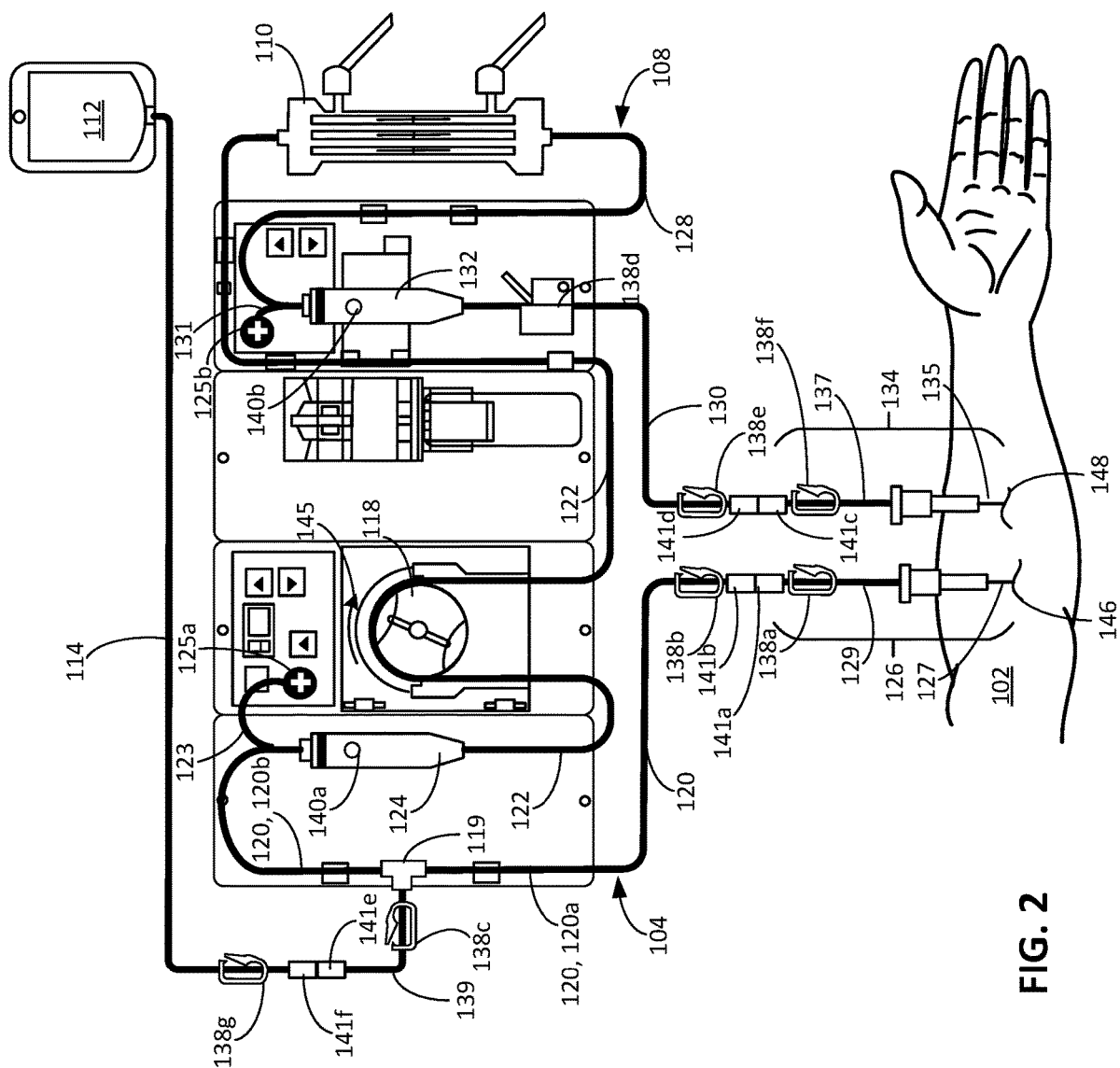
FIG. 2 illustrates a configuration of fluid lines forming an extracorporeal blood circuit during an extracorporeal treatment of a patient.
Figure 3:
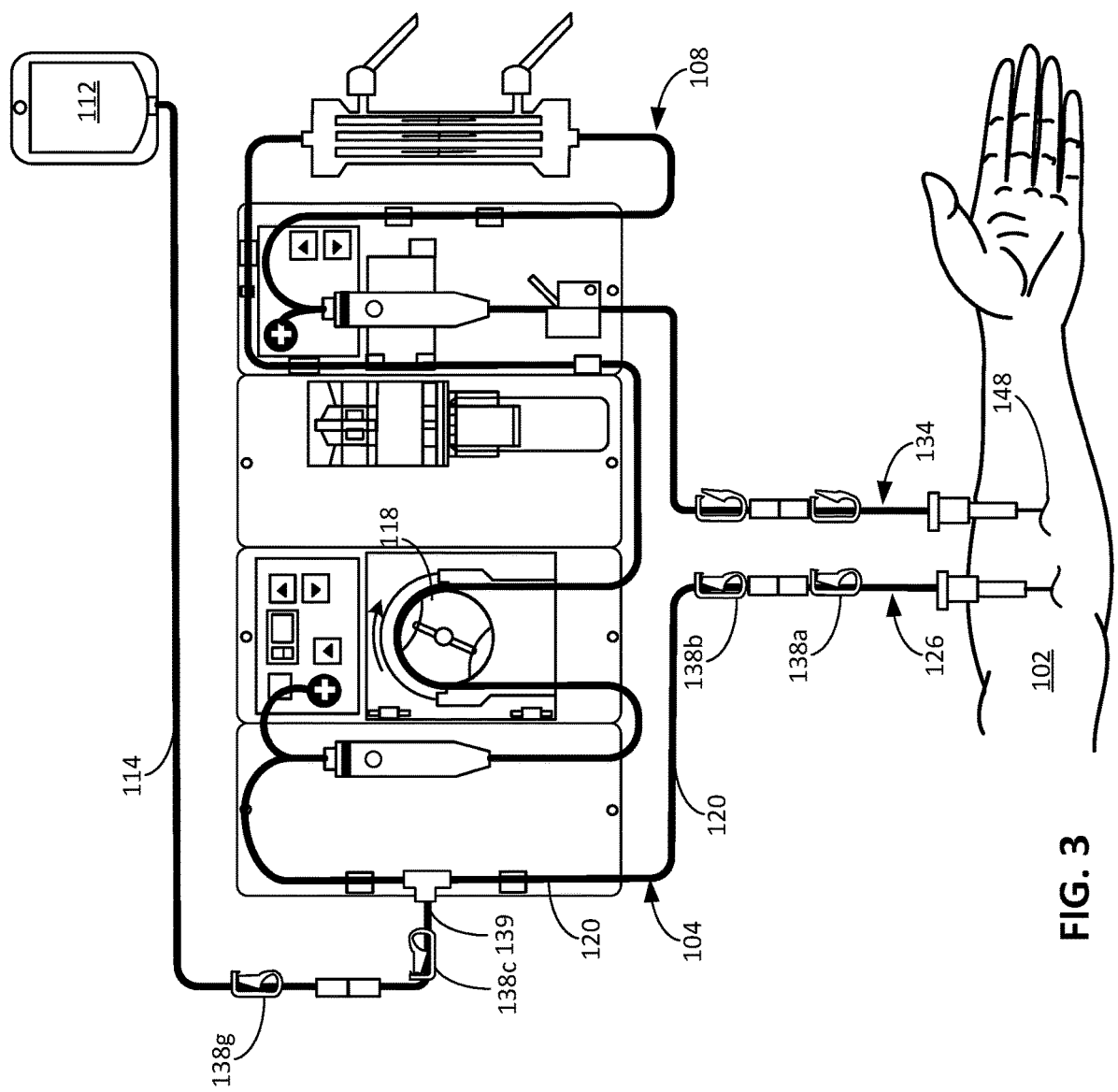
FIG. 3 illustrates a configuration of the fluid lines of FIG. 2 after the extracorporeal treatment is complete and after a clamp along an arterial line set is placed in a closed position.

Referring to FIG. 2, the arterial line set 104 includes an arterial access line 120, an arterial line 122, and an arterial drip chamber 124. One end of the arterial access line 120 is connected to a top of the arterial drip chamber 124, and the other end of the arterial access line 120 is connectable to an arterial needle assembly 126. The arterial access line 120 includes a first portion 120a and a second portion 120b each connected to a fluid adapter 119 of the arterial line set 104.

The arterial line 122 extends from the bottom of the arterial drip chamber 124 to the dialyzer 110. The arterial drip chamber 124 is positioned along the arterial access line 120. A pressure transducer 125a is connected to the arterial drip chamber 124 via a pigtail line 123 extending from the arterial drip chamber 124 and is configured to detect a fluid pressure within the arterial drip chamber 124.

The arterial needle assembly 126 includes a needle 127 that is insertable into the patient 102 and a fluid line 129 that is connectable to the arterial access line 120. A manually operable connector 141a at the end of the fluid line 129 is configured to be connected to a manually operable connector 141b at the end of the first portion 120a of the arterial access line 120. Like the arterial line set 104, the arterial needle assembly 126 can be a single-use disposable component that is discarded after the end of the extracorporeal treatment. During an extracorporeal treatment, the arterial needle assembly 126 is connected to the arterial access line 120 using the connectors 141a, 141b. The needle 127 of the arterial needle assembly 126 is inserted into the patient 102 to enable blood to be drawn into the arterial line set 104 from the patient 102.

The venous line set 108 includes a venous line 128, a venous access line 130, and a venous drip chamber 132. The venous line 128 extends from the dialyzer 110 to a top of the venous drip chamber 132. One end of the venous access line 130 is connected to a bottom of the venous drip chamber 132, and the other end of the venous access line 130 is connected to a venous needle assembly 134. A pressure transducer 125b is connected to the venous drip chamber 132 via a pigtail line 131 extending from the venous drip chamber 132 and is configured to detect a fluid pressure within the venous drip chamber 132.

During an extracorporeal treatment, the venous needle assembly 134 is connected to the venous access line 130. The venous needle assembly 134 includes a needle 135 that is insertable into the patient 102 to enable filtered blood, e.g., blood that has travelled through the dialyzer 110, to be returned to the patient 102 through the venous line set 108. The venous needle assembly 134 further includes a fluid line 137 to be connected to the venous access line 130. A manually operable connector 141c at the end of the fluid line 137 is configured to be connected to a manually operable connector 141d at the end of the venous access line 130.

The arterial line set 104 and the venous line set 108 form an extracorporeal blood circuit through which the blood of the patient 102 circulates. The blood pump 118, when operated during the extracorporeal treatment, causes blood to flow from the patient 102, through the extracorporeal blood circuit and the dialyzer 110, and then back into the patient 102 after filtration has occurred in the dialyzer 110. The blood pump 118 generates a negative pressure in the arterial access line 120. A signal generated by the pressure transducer 125a can be indicative of this negative pressure. The blood pump 118 generates a positive pressure in the arterial line 122 and in the venous line set 108. For example, the blood pump 118 generates a negative pressure in a portion of the arterial line 122 upstream of the blood pump 118 and generates a positive pressure in a portion of the arterial line 122 downstream of the blood pump 118. A signal generated by the pressure transducer 125b can be indicative of the positive pressure in the downstream portion of the arterial line 122 and the venous line set 108.

When flow through the arterial line set 104 is inhibited, e.g., due to operation of flow regulators (e.g., clamps) that interact with the arterial line set 104, negative pressure generated in the arterial line set 104 can be maintained until the flow regulators are operated to allow blood to flow through the arterial line set 104 and the venous line set 108. When the flow regulators are operated to allow the blood to flow, as described herein, the negative pressure causes blood to be drawn further into the arterial line set 104 for reinfusion back to the patient 102.

Disposable portions of the extracorporeal system 100 include the fluid line 114 and the fluid source 112. The fluid line 114 is connected to the arterial line set 104 along the arterial line 122. For example, a port 139 of the arterial line set 104 extends from the fluid adapter 119 of the arterial line set 104 and is connectable to the fluid source 112, e.g., through the fluid line 114. An end of the port 139 includes a manually operable connector 141e configured to be connected to a manually operable connector 141f at an end of the fluid line 114. The connectors 141a-141f described herein can be threaded connectors that connect to one another through a threaded engagement, a snap fit engagement, or another appropriate engagement mechanism.

The fluid line 114 is connected to the fluid source 112 such that fluid from the fluid source 112 can be drawn into the arterial line set 104 when the fluid line 114 is connected to the port 139 of the arterial line set 104. The fluid source 112 can include, for example, one or more of a priming solution, a substitution fluid, saline, or other medical fluids. The fluid source 112 is, for example, a saline bag that can be hung from a vertically extending member 136 (shown in FIG. 1) that positions the fluid source 112 above the patient 102. The fluid source 112 is positioned above the patient 102 such that flow from the fluid source 112 to the patient 102, e.g., through the arterial line set 104 and the venous line set 10, can be driven by gravity.

The machine 106 further includes one or more flow regulators engageable with the arterial line set 104, the venous line set 108, and the fluid line 114. The flow regulators can be manually operable, electronically addressable, or both. In the embodiment illustrated in FIG. 2, for example, the machine 106 includes clamps 138a-138g, the clamps 138a-138f being manually operable and the clamp 138d being automated. The clamp 138a is positioned to engage the fluid line 129 of the arterial needle assembly 126. The clamp 138b is positioned to engage the arterial access line 120. The clamp 138c is positioned to engage the port 139 of the arterial line set 104. The clamp 138d is positioned to engage the portion of the venous access line 130 proximate the venous drip chamber 132. The clamp 138e is positioned to engage the portion of the venous access line 130 proximate the venous needle assembly 134. The clamp 138f is positioned to engage the fluid line 137 of the venous needle assembly 134. The clamp 138g is positioned to engage the fluid line 114. The clamps 138a-138g can be independently actuated to control fluid flows through the arterial line set 104, the venous line set 108, and the fluid line 114.

In some implementations, the machine 106 includes one or more fluid flow sensors. For example, a fluid flow sensor 140a can be positioned to detect fluid flow through the arterial drip chamber 124, and a fluid flow sensor 140b can be positioned to detect fluid flow through the venous drip chamber 132. The fluid flow sensors 140a, 140b can be optical sensors responsive to drops of fluid through the arterial drip chamber 124 and the venous drip chamber 132, respectively. The fluid flow sensors 140a, 140b can detect flow rates of fluid flowing through the arterial drip chamber 124 and the venous drip chamber 132, respectively. In addition, the fluid flow sensors 140a, 140b can distinguish between fluids having different opacities, such as blood and saline. For example, during operation of the blood pump 118, the type of fluid flowing through the arterial drip chamber 124 and the venous drip chamber 132 may vary depending on the stage of the extracorporeal treatment or the blood reinfusion process. The fluid flow sensors 140a, 140b can distinguish between the different types of fluid and provide the controller 144 with a signal indicative of a current stage of the extracorporeal treatment or the blood reinfusion process.

Whereas the arterial line set 104, the dialyzer 110, and the venous line set 108 form the extracorporeal blood circuit, the machine 106 includes components that form a dialysis fluid circuit with the dialyzer 110. These components include dialysate lines located inside the machine 106 and thus are not visible in FIG. 1. The extracorporeal blood circuit and the dialysis fluid circuit extend alongside one another through the dialyzer 110 such that the blood and the dialysis fluid flow adjacent one another through the dialyzer 110 during an extracorporeal treatment. Flow of the blood and the dialysis fluid through the dialyzer 110 filters the blood by causing waste substances from the blood to diffuse into the dialysis fluid.

In some implementations, the machine 106 also includes an ultrafiltration pump 142 (shown in FIG. 1) to draw liquid, e.g., water, from the blood circulating through the dialyzer 110. The ultrafiltration pump 142 generates a pressure on the dialysis fluid circuit, thereby creating a pressure differential between the dialysis fluid circuit and the extracorporeal blood circuit. This pressure differential can cause liquid, e.g., water, to be withdrawn from the blood of the patient 102 through the dialyzer 110. During the ultrafiltration process, water is drawn from the extracorporeal blood circuit, through the dialyzer, and into a waste line of the dialysis fluid circuit.

The machine 106 also includes a dialysis fluid pump 143 (shown in FIG. 1) operably connected to the dialysis fluid circuit. During an extracorporeal treatment, the dialysis fluid pump 143 is operated to circulate the dialysis fluid through the dialysis fluid circuit. The dialysis fluid pump 143 draws dialysis fluid from a dialysis fluid source, through the dialyzer, and then into a dialysis fluid drain.

The machine 106 further includes a controller 144 (shown in FIG. 1) operably connected to the blood pump 118, the pressure transducers 125a, 125b, the fluid flow sensors 140a, 140b, the ultrafiltration pump 142, and the dialysis fluid pump 143. The controller 144 automatically controls operations of the blood pump 118 during the extracorporeal treatment and the blood reinfusion process. As described herein, in some implementations, the controller 144 operates the blood pump 118 based on flow rates detected by one or more of the fluid flow sensors 140a, 140b. Alternatively or additionally, the controller 144 operates the blood pump 118 based on pressures detected by one or more of the pressure transducers 125a, 125b.

In some implementations, a user interface system 150 is operable by the operator to monitor and to control operations of the machine 106. The user interface system 150 includes a touchscreen 151 and a display 152. The operator can manually operate the touchscreen 151 to control operations of the machine 106, and the display 152 can provide visual indications to the operator. The user interface system 150 is integral to the machine 106.

Examples of extracorporeal treatments and blood reinfusion processes are described with respect to FIGS. 2-6. FIG. 2 illustrates a portion of the extracorporeal system 100 when the patient 102 is undergoing an extracorporeal treatment. Before the extracorporeal treatment is initiated, a human operator, e.g., a clinician, a nurse, or other clinical personnel, positions the arterial line set 104, arranges the venous line set 108, the fluid line 114, and the fluid source 112 in preparation for the extracorporeal treatment. The operator positions the arterial line set 104 such that the blood pump 118 engages a portion of the arterial line 122 and connects the fluid line 114 to the port 139 of the arterial line set 104 using the connectors 141e, 141f. The operator also mounts the arterial drip chamber 124 and the venous drip chamber 132 adjacent the fluid flow sensors 140a, 140b to enable the fluid flow sensors 140a, 140b to detect fluid flow through the arterial drip chamber 124 and the venous drip chamber 132, respectively. The operator mounts the dialyzer 110 to the machine 106 and connects the arterial line 122 and the venous line 128 to the dialyzer 110.

The operator then places the arterial line set 104 and the venous line set 108 in fluid communication with the circulatory system of the patient 102. The operator connects the fluid line 129 of the arterial needle assembly 126 to the arterial access line 120 using the manually operable connectors 141a, 141b. The operator also connects the fluid line 137 of the venous needle assembly 134 to the venous access line 130 using the manually operable connectors 141c, 141d. The operator further inserts the arterial needle assembly 126 (connected to the arterial access line 120) into an arterial access 146 of the patient 102, and inserts the venous needle assembly 134 (connected to the venous access line 130) into a venous access 148 of the patient 102. The arterial needle assembly 126, the arterial line set 104, the venous line set 108, the venous needle assembly 134, and the dialyzer 110 thus form an extracorporeal circuit connected to the circulatory system of the patient 102. For example, the arterial line set 104 and the venous line set 108 are in fluid communication with one another through the dialyzer 110 and are both in fluid communication with the circulatory system of the patient 102.

The operator also connects the fluid line 114 to the port 139 of the arterial line set 104 using the manually operable connectors 141e, 141f. This places the fluid source 112 in fluid communication with the arterial line set 104 and hence the extracorporeal circuit. For example, the fluid line 114 is connected in parallel with the arterial access line 120 such that negative pressure generated along the arterial line 122 draws blood from the patient 102 as well as fluid through the fluid line 114 into the arterial line 122. The operator positions the fluid line 129 of the arterial needle assembly 126 to enable the clamp 138a to be engaged with the fluid line 129. The arterial line set 104 is positioned to enable the clamp 138b to be engaged with the fluid line 129 of the arterial needle assembly 126. The arterial line set 104 is also positioned to enable the clamp 138c to be engaged with the port 139.

The operator positions the venous line set 108 to enable the clamp 138d to be engaged with an outlet of the venous access line 130 extending from the venous drip chamber 132. The venous line set 108 is also positioned to enable the clamp 138e to be engaged with a portion of the venous access line 130 between the outlet from the venous drip chamber 132 and the fluid line 137 of the venous needle assembly 134. The venous needle assembly 134 is positioned to enable the clamp 138f to be engaged with the fluid line 137 of the venous needle assembly 134. The operator positions the fluid line 114 to enable the clamp 138g to be engaged with the fluid line 114.

By positioning these portions of the arterial line set 104, the venous line set 108, and the fluid line 114 in this manner, fluid flow through each of the fluid line 114, the arterial needle assembly 126, the arterial line set 104, the venous needle assembly 134, and the venous line set 108 can be independently controllable through operation of the clamps 138a-138g. In preparation for the extracorporeal treatment, each of the clamps 138a-138g are placed in open positions such that flow is allowed through each of the arterial needle assembly 126, the arterial line set 104, the venous line set 108, the venous needle assembly 134, and the fluid line 114.

The operator connects a dialysis fluid source to the dialysis fluid circuit to enable dialysis fluid to be circulated through the dialyzer 110. The operator also connects a drain line to the dialysis fluid circuit so that spent dialysis fluid, e.g., dialysis fluid that has flown through the dialyzer 110 and that has received waste substances from the blood, can be discarded into a drain through the drain line. The drain line can further receive ultrafiltrate drawn from the blood during the ultrafiltration process facilitated by operation of the ultrafiltration pump 142.

After the operator has set up the arterial line set 104, the venous line set 108, and the fluid line 114 and has set up the dialysis fluid circuit, the operator initiates the extracorporeal treatment, thereby triggering automated control of the extracorporeal treatment by the controller 144. During the extracorporeal treatment, the blood pump 118 is operated to circulate blood through the dialyzer 110. The controller 144 can control the blood pump 118 through feedback control based on pressures detected by the pressure transducers 125a, 125b or based on flow rates detected by the fluid flow sensors 140a, 140b. The blood pump 118 is driven such that blood in the arterial line set 104 is drawn from the patient 102 and directed toward the dialyzer 110 and the venous line set 108. For example, the blood pump 118 generates a negative pressure along the portion of the arterial line set 104 between the patient 102 and the blood pump 118 and a positive pressure along the portion of the arterial line set 104 between the blood pump 118 and the dialyzer 110 and along the venous line set 108. If the blood pump 118 is a peristaltic pump, the blood pump 118 is rotated in a rotational direction 145, thereby generating this pressure differential to circulate blood through the extracorporeal blood circuit.

The dialysis fluid pump 143 is operated to circulate dialysis fluid through the dialyzer 110. Waste substances from the blood diffuse into the dialysis fluid. In addition, in some implementations, the ultrafiltration pump 142 is operated to draw excess fluid from the extracorporeal blood circuit into the dialysis fluid circuit.

After the end of the extracorporeal treatment, an operation to deactivate the blood pump 118, the dialysis fluid pump 143, and the ultrafiltration pump 142 is initiated. For example, referring to FIG. 3, the controller 144 automatically stops the extracorporeal treatment after predetermined criteria are fulfilled, e.g., a certain amount of time has elapsed or a certain amount of ultrafiltrate has been removed from the blood. The controller 144 ceases operation of the blood pump 118, the dialysis fluid pump 143, and the ultrafiltration pump 142. After the operation of the pumps 118, 142, 143 has been stopped, blood drawn from the patient 102 during the extracorporeal treatment may be present in the arterial line set 104 and the venous line set 108. During the blood reinfusion process, this blood is returned to the patient 102 through the venous access 148 of the patient 102.

The blood reinfusion process is then initiated to return residual blood in the arterial line set 104 and the venous line set 108 to the patient 102. For example, the operator initiates the blood reinfusion process by operating the user interface system 150. Upon initiation of the blood reinfusion process, instructions, e.g., audible or visual instructions, are presented to the operator to perform particular operations for infusing the blood remaining in the arterial line set 104 and the venous line set 108. The instructions are presented through the display 152 of the user interface system 150. In some implementations, after the operator completes a set of operations for the blood reinfusion process, the operator operates the touchscreen 151 of the user interface system 150 to cause the display 152 to provide instructions for a subsequent set of operations.

For the blood reinfusion process, the operations performed by the operator include clamping and unclamping one or more portions of the arterial needle assembly 126, the arterial line set 104, the venous line set 108, the venous needle assembly 134, the fluid line 114, or a combination of these fluid line systems. For example, after the blood reinfusion process is initiated, the operations include placing each of the clamps 138a-138c and 138g in the closed position. The clamps 138a, 138b are actuated to inhibit flow through the arterial needle assembly 126 and the arterial access line 120. The clamp 138c is actuated to inhibit flow through the port 139 of the arterial line set 104, for example, from the fluid line 114. In addition, the clamp 138g is actuated to engage the fluid line 114 to inhibit fluid flow through the fluid line 114 from the fluid source 112.

Figure 4:
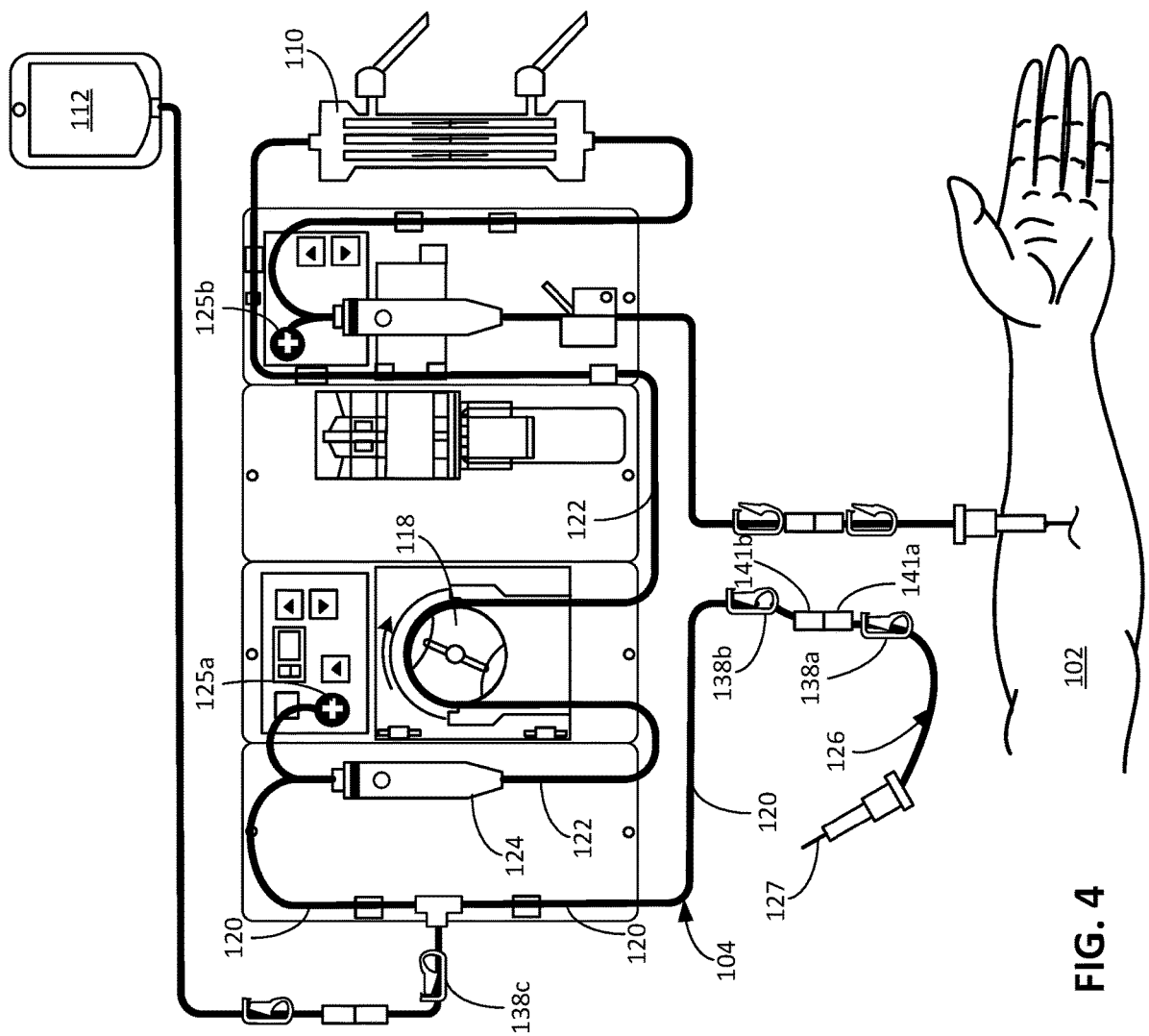
FIG. 4 illustrates a configuration of the fluid lines of FIG. 3 after an arterial needle is removed from the patient and after the clamp along the arterial line set is placed in the closed position.

Referring to FIG. 4, the arterial needle assembly 126 with the arterial access line 120 is removed from fluid communication with the patient 102. For example, the arterial needle assembly 126 is physically disconnected from the patient 102. Blood flow out of the arterial needle assembly 126, when removed from the patient 102, is inhibited through the negative pressure caused by the clamped line. The controller 144 then initiates operation of the blood pump 118. Similar to its operation during the extracorporeal blood treatment, the blood pump 118 is operated to generate a negative pressure along the portion of the arterial line 122 extending from the arterial drip chamber 124 to the blood pump 118 and to generate positive pressure along the portion of the arterial line 122 extending from the blood pump 118 to the dialyzer 110. Because the clamps 138a-138c are in the closed position, the pressure differential does not cause blood to flow through the extracorporeal blood circuit. The pressure differential is maintained until one of the clamps 138a-138c are placed in the open position to enable the flow of blood to occur.

The controller 144 operates the blood pump 118 based on pressures detected by the pressure transducers 125a, 125b. For example, the blood pump 118 can be operated to generate a pressure between 150 mmHg and 250 mmHg, e.g., between 175 mmHg and 225 mmHg or 190 mmHg and 210 mmHg, at the arterial drip chamber 124. This is a negative pressure and thus corresponds to a pressure that tends to draw the fluid within the portion of the arterial line set 104 between the arterial needle assembly 126 and the blood pump 118 toward the blood pump 118. In some cases, the controller 144 continues operating the blood pump 118 until the pressure detected by the pressure transducer 125a reaches a predefined pressure between 150 mmHg and 250 mmHg, e.g., between 175 mmHg and 225 mmHg, between 190 mmHg and 210 mmHg, or about 200 mmHg.

To draw blood out of the arterial needle assembly 126 and the arterial access line 120 before the arterial needle assembly 126 is disconnected from the arterial line set 104, the operator unclamps the arterial access line 120. For example, the clamps 138a and 138b are placed in the open position. When the arterial access line 120 is unclamped, fluid is drawn into the arterial access line 120 further into the arterial line set 104 in a direction away from the end of the arterial access line 120 connectable to the arterial access 146 of the patient 102. This allows blood within the arterial needle assembly 126 to be collected for reinfusion into the patient 102, and also allows blood within the arterial access line 120 to be collected for reinfusion into the patient 102 without having to disconnect the arterial needle assembly 126 from the arterial line set 104.

The negative pressure generated by the blood pump 118 causes the blood in the arterial needle assembly 126, the arterial access line 120, and the portion of the arterial line 122 between the arterial access line 120 and the arterial drip chamber 124 to flow into the arterial drip chamber 124. The arterial drip chamber 124 has sufficient interior volume to accommodate and hold the blood after the negative pressure causes the blood to be drawn into the arterial drip chamber 124. The negative pressure can ensure that blood is immediately drawn into the arterial drip chamber 124 when the clamp 138b is opened. This negative pressure can thus prevent blood from leaking out of the arterial line set 104 into the environment when the clamps 138a, 138b are placed in the open positions. The negative pressure creates a suction that prevents blood from leaking out the arterial line set 104 through the arterial needle assembly 126 such that the blood can be recovered for reinfusion and stored in the arterial drip chamber 124. In addition, the suction draws the blood from the arterial needle assembly 126 into the arterial access line 120 and into the arterial drip chamber 124 such that, after the pressure within the arterial line set 104 equilibrates with respect to the pressure of the environment, the arterial needle assembly 126 substantially only contains air.

The operator unclamps the arterial access line 120 as the operator removes the arterial needle assembly 126 from the patient 102 such that blood within the arterial needle assembly 126 can be drawn further into the arterial line set 104 with reduced risk of blood leakage through the arterial needle 127. In addition, rather than having to activate the blood pump 118 to cause the blood to be drawn further into the arterial line set 104, the operator can operate the clamps 138a, 138b, which are easily accessible by hands of the operator when the operator is manually removing the arterial needle assembly 126 from the patient 102.

After the clamp 138b is placed in the open position and the blood is drawn into the arterial drip chamber 124, the operator disconnects the arterial needle assembly 126 from the arterial line set 104 by disconnecting the connectors 141a, 141b from one another. The operator can then discard the arterial needle assembly 126. The arterial needle assembly 126 is thus disconnected from the arterial line set 104 after the blood within the arterial needle assembly 126 is drawn into the arterial drip chamber 124. The absence of blood within the arterial needle assembly 126 can reduce the risk of inadvertent blood leakage that can occur during the process of disconnecting the arterial needle assembly 126 from the arterial line set 104, thereby reducing the risk of exposing the operator to the blood of the patient 102.

Figure 5:
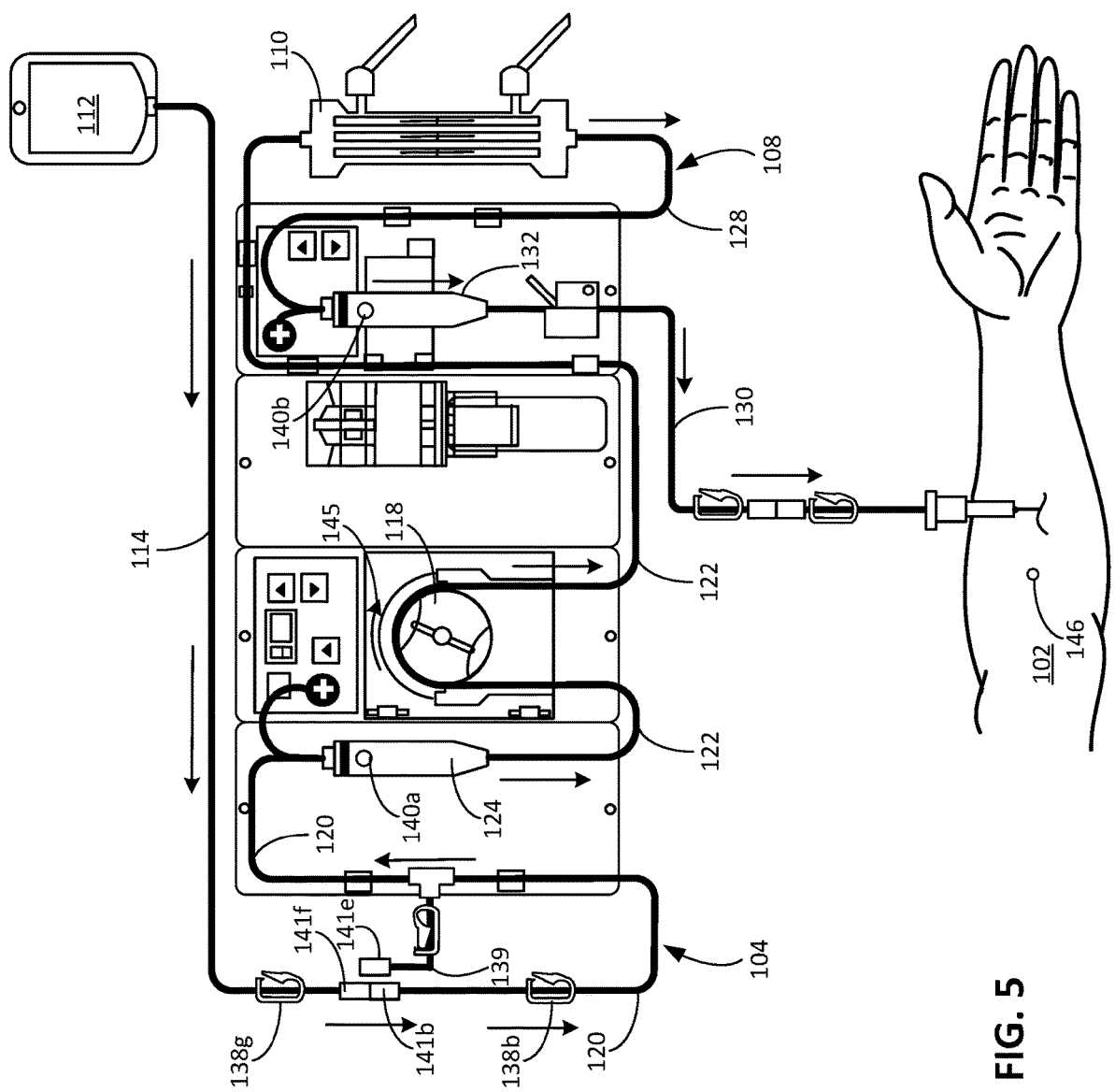
FIG. 5 illustrates a configuration of the fluid lines of FIG. 4 after an arterial access line of the arterial line set is connected to a fluid line connected to a fluid source and after the clamp along the arterial line set is placed in the open position.

Referring to FIG. 5, the fluid line 114 is disconnected from the port 139, e.g., the connectors 141e, 141f are disconnected from one another. The connector 141f is then connected to the connector 141b on the arterial access line 120, thereby connecting the fluid line 114 to the arterial access line 120. The clamp 138g is then placed in the open position such that the fluid line 114 is in fluid communication with the arterial line set 104. For example, the fluid line 114 is connected to the arterial line set 104 such that the fluid line 114, the arterial access line 120, and the arterial line 122 are in series with one another.

The fluid line 114, the arterial line set 104, and the venous line set 108 are now connected in series with one another such that fluid from the fluid source 112 sequentially flows through the fluid line 114, the arterial line set 104, and the venous line set 108 to flush residual blood from the lines and return the blood to the patient 102. Fluid from the fluid source 112 can thus flow through an entire length of the arterial access line 120 to cause the blood remaining the arterial access line 120 to flow through the arterial line set 104, into the venous line set 108, and into the patient 102.

Operation of the blood pump 118 can then be initiated to drive the fluid from the fluid source 112 through the fluid line 114, the arterial line set 104, and the venous line set 108. While the height of the fluid source 112 relative to the patient 102 can cause gravity-driven flow of the fluid from the fluid source 112 through the arterial line set 104, this flow can be difficult to control absent electronically addressable flow regulators, pumps, or other fluid flow instrumentation. The blood pump 118 can be controlled in a manner to enable precise and accurate return of the blood.

The operator initiates the operation of the blood pump 118, for example, through a user input into the user interface device. In this regard, fluid from the fluid source 112 is drawn through the fluid line 114, through the arterial access line 120, and then through the arterial line 122 when the blood pump 118 is driven in the rotational direction 145. The blood then travels through the dialyzer 110, through the venous line 128, and then through the venous access line 130 and into the patient 102. The blood in the arterial line set 104 and the venous line set 108 is thus returned to the patient 102 through the venous access line 130. By using pressure generated by the blood pump 118 of the machine 106, the operator can avoid having to connect an external pressure source to the arterial line set 104 to generate a positive pressure to cause blood flow.

The controller 144 automatically stops operation of the blood pump 118. The fluid pump operation can be, for example, stopped based on signals from the fluid flow sensors 140a, 140b associated with the arterial drip chamber 124 and the venous drip chamber 132. For example, the fluid flow sensors 140a, 140b can distinguish blood from fluid delivered by the fluid source 112 (e.g., saline). The controller 144 automatically stops the operation of the blood pump 118 in response to detecting that blood is no longer flowing through both the arterial drip chamber 124 and the venous drip chamber 132 for a predefined duration of time between 0 seconds and 15 seconds, e.g., between 0 and 5 seconds, between 5 seconds and 15 seconds, about 7.5 and 12.5 seconds, about 10 seconds. The blood pump 118 remains active for the predefined duration of time so that the venous access line 130 can also be flushed with fluid from the fluid source 112.

In some cases, the controller 144 first receives a signal from the fluid flow sensor 140a indicating that blood is no longer flowing through the arterial drip chamber 124 and then receives a subsequent signal from the fluid flow sensor 140b indicating that blood is no longer flowing through the venous drip chamber 132. The signal from the fluid flow sensor 140b indicates the arterial line set 104 and through the venous line 128 have been flushed with fluid from the fluid source 112. Upon receiving the signal from the fluid flow sensor 140b, the controller 144 continues operation of the blood pump 118 for the predefined duration of time and then stops the fluid pump operation after the predefined duration of time has elapsed. Alternatively or additionally, the controller 144 monitors the signal from the fluid flow sensor 140b and stops the operation of the blood pump 118 upon determining that fluid from the fluid source 112 has been flowing through the venous drip chamber 132 for the predefined duration of time.

Figure 6:
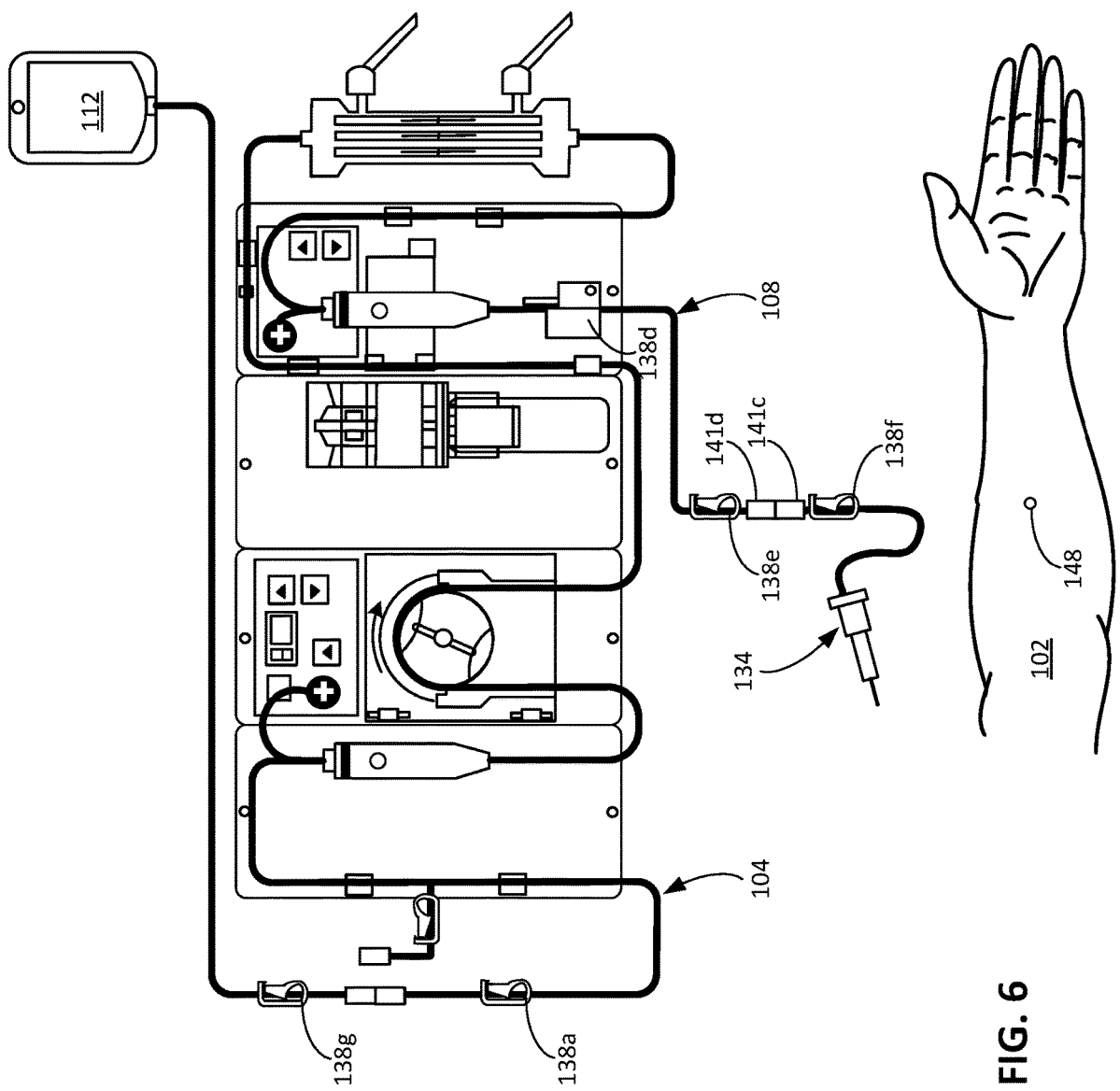
FIG. 6 illustrates a configuration of the fluid lines of FIG. 5 after a venous access line of a venous line set is removed from the patient and after a clamp along the venous line set is placed in a closed position.

In addition to stopping the operation of the blood pump 118, as shown in FIG. 6, the controller 144 automatically places the clamp 138d in the closed position to inhibit further flow of fluid through the venous line set 108. This can prevent excessive fluid from being infused into the patient 102.

Referring to FIG. 6, after the residual blood in the arterial line set 104 and the venous line set 108 has been infused into the patient 102 and the operation of the blood pump 118 has stopped, the clamps, 138a, 138e, 138f, and 138g are placed in the closed position to prevent fluid from flowing out of the arterial line set 104 or out of the venous line set 108. The connector 141c of the venous needle assembly 134 is disconnected from the connector 141d of the venous line set 108. The venous needle assembly 134 is then removed from the venous access 148 and can then be discarded.

A number of implementations have been described. Nevertheless, it will be understood that various modifications may be made. For example, while the extracorporeal medical fluid treatment system 100 is described as a dialysis system, in some examples, the extracorporeal medical fluid treatment system 100 can perform another type of blood treatment procedure. For example, the blood treatment procedure performed by the extracorporeal medical fluid treatment system 100 can include blood filtration, hemofiltration, blood donation, blood detoxification, apheresis, cardiac catheterizations, among other blood treatment procedures.

While the arterial line set 104 is described as including the arterial drip chamber 124, in some implementations, the arterial line set 104 does not have a drip chamber. Rather, the arterial line set 104 includes the arterial access line 120 directly connected to the arterial line 122. Alternatively or additionally, the arterial line set 104 includes a continuous arterial line extending from the dialyzer 110 to the arterial needle assembly 126.

While fluid from the fluid source 112 is described as being driven by gravity to flow into the arterial line set 104, in some cases, an active pumping mechanism is provided to cause the fluid to flow into the arterial line set 104. For example, the machine 106 further includes a fluid pump, e.g., a peristaltic pump, to drive the fluid from the fluid source 112 into the arterial line set 104.

While the blood pump 118 has been described as a peristaltic pump, other types of pumps can be used. For example, the blood pump 118 can alternatively be a roller pump, a linear pump, a syringe pump, or other appropriate types of pumps. In addition, the pump 118, in some implementations, is operated to drive a fluid other than blood through the arterial line set 104. For example, the fluid driven by the pump 118 can include saline, plasma, dialysate, or another medical fluid.

While the user interface system 150 has been described as including the touchscreen 151 and the display 152, in other implementations, the user interface system 150 includes another appropriate type of user input device or another appropriate type of user output device. For example, the user input device includes a keyboard, a mouse, a microphone, or other user input device. The user output device includes a speaker, a computer monitor, or other appropriate computing user output device. Furthermore, although the user interface system 150 is described as being integral to the machine 106, in some implementations, the user interface system 150 is a remote computing device in wireless communication with the machine 106, While fluid flow through the arterial line set 104, the venous line set 108, or the fluid line 114 is described as being inhibited through operation of the clamps 138a-138g, in some implementations, other flow regulators are used to regulate fluid flows through the fluid lines. For example, the arterial line set 104, the venous line set 108, or the fluid line 114 can include manually operable valves that can be opened or closed to allow or prevent fluid from flowing through portions of the arterial line set 104, the venous line set 108, or the fluid line 114. Furthermore, although the clamps 138a-138f are described as being manually operated by the operator, in some implementations, these flow regulators are electronically addressable devices that can be operated by the controller 144. In this regard, the operations to clamp and unclamp portions of the arterial line set 104, the venous line set 108, or the fluid line 114 can be controlled by the controller 144.

While the arterial needle assembly 126 is described with respect to FIG. 4 as being disconnected from the patient 102, in some implementations, fluid communication between the arterial needle assembly 126 and the patient 102 is removed in another manner. For example, in some implementations, a catheter clamp is engaged to the arterial needle assembly 126 to inhibit blood flow from the patient 102 into the arterial needle assembly 126.

While operations of the pumps 118, 142, 143 are described as being stopped in an automated manner facilitated by the controller 144 at the end of the extracorporeal treatment, in some implementations, the operator manually stops operations of the pumps 118, 142, 143. For example, the operator provides a user input through the user interface system 150 to initiate the operation to deactivate the pumps 118, 142, 143.

While the controller 144 is described as operating the blood pump 118 based on detected pressures, in some implementations, other criteria are used to control operations of the blood pump 118. In some cases, the controller 144 operates the blood pump 118 for a predefined amount of time. For example, the blood pump 118 can be activated for 5 to 15 seconds, e.g., between 7.5 and 12.5 seconds, 9 and 11 seconds, or about 10 seconds. In some cases, the blood pump 118, when operated, drives fluid through the arterial line set 104 at a flow rate of 100 to 200 mm/min, e.g., between 125 and 175 mm/min or about 150 mm/min.

While both clamps 138a and 138b are described as being placed in the open position to allow the negative pressure to draw the blood into the arterial drip chamber 124 during the blood reinfusion process, in some implementations, only one of the clamps 138a, 138b are present. For example, the clamp 138a alone can be placed in the open position to allow the negative pressure draw the blood from the arterial needle assembly 126 and the arterial access line 120 into the arterial drip chamber 124.

While both of the fluid flow sensors 140a, 140b are described in connection to the blood reinfusion process, in some implementations, the controller 144 only monitors the fluid flow sensor 140b to determine whether to stop the operation of the blood pump 118. The controller 144 stops the operation of the blood pump 118 after determining that fluid from the fluid source 112 has been flowing through the venous drip chamber 132 for the predefined duration of time or after determining that blood has not been flowing through the venous drip chamber 132 for the predefined duration of time.

In some implementations, the controller 144 automatically stops the operation of the blood pump 118 after a predefined duration of time has elapsed after initiation of the blood pump 118. This predefined duration of time is between, for example, 3 minutes and 5 minutes, e.g., between 3.8 and 4.2 minutes, between 3.9 minutes and 4.1 minutes, or about 4 minutes.

Dialysis fluid flows through the dialysis fluid circuit during an extracorporeal treatment. In some implementations, the dialysis fluid includes dialysate, saline, water, sodium chloride, sodium bicarbonate, sodium acetate, calcium chloride, potassium chloride, magnesium chloride, or any combination of these substances.

The extracorporeal blood treatment systems described herein can be controlled, at least in part, using one or more computer program products, e.g., one or more computer programs tangibly embodied in one or more information carriers, such as one or more non-transitory machine-readable media, for execution by, or to control the operation of, one or more data processing apparatus, e.g., a programmable processor, a computer, multiple computers, and/or programmable logic components.

Operations associated with controlling the extracorporeal blood treatment systems described herein can be performed by one or more programmable processors executing one or more computer programs to perform the functions described herein. A computer program can be written in any form of programming language, including compiled or interpreted languages, and it can be deployed in any form, including as a stand-alone program or as a module, component, subroutine, or other unit suitable for use in a computing environment. Control over all or part of the extracorporeal blood treatment systems described herein can be implemented using special purpose logic circuitry, e.g., an FPGA (field programmable gate array) and/or an ASIC (application-specific integrated circuit).

The controllers described herein can include one or more processors. Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer include one or more processors for executing instructions and one or more storage area devices for storing instructions and data. Generally, a computer will also include, or be operatively coupled to receive data from, or transfer data to, or both, one or more machine-readable storage media, such as mass PCBs for storing data, e.g., magnetic, magneto-optical disks, or optical disks. Machine-readable storage media suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

Other implementations are within the scope of the claims.

What is claimed is:

1. A method comprising:
   clamping an access line of an arterial line set, the arterial line set comprising an arterial line connected to the access line, and the access line being connectable to an arterial access of a patient such that the access line is between a fluid pump and the arterial access;
   after clamping the access line, initiating an operation to generate negative pressure, using the fluid pump, in a portion of the arterial line set between the fluid pump and the access line;
   after generating the negative pressure in the portion of the arterial line set, unclamping the access line such that the negative pressure generated in the portion of the arterial line set before unclamping the access line draws fluid in the access line further into the arterial line set in a direction away from an end of the access line that is connectable to the arterial access of the patient; and
   initiating an operation of the fluid pump engaged with the arterial line set such that the fluid in the arterial line set is infused into the patient through a venous line set.

2. The method of claim 1, further comprising, after an end of an extracorporeal blood treatment and before clamping the access line, initiating an operation to deactivate an ultrafiltration pump and to deactivate the fluid pump.

3. The method of claim 1, further comprising clamping a port of the arterial line set, the port being connectable to a fluid source.

4. The method of claim 3, wherein the operation to generate the negative pressure is initiated while the port and the access line of the arterial line set are clamped.

5. The method of claim 1, further comprising:
   disconnecting a port of the arterial line set from a fluid source; and
   connecting the access line to the fluid source.

6. The method of claim 3, further comprising clamping a fluid line connecting the fluid source to the port of the arterial line set before disconnecting the port.

7. The method of claim 1, further comprising removing an arterial needle, connected to the access line, from the arterial access, wherein the operation to generate the negative pressure is initiated while the arterial needle is removed.

8. The method of claim 7, further comprising disconnecting the arterial needle from the access line after unclamping the access line.

9. The method of claim 1, wherein the operation to generate the negative pressure in the portion of the arterial line set is initiated to draw the fluid in the arterial line set into a drip chamber of the arterial line set.

10. The method of claim 1, further comprising connecting the access line to a fluid source, wherein the access line is unclamped before the fluid pump is operated to infuse the fluid and after the access line is connected to the fluid source, thereby causing another fluid from the fluid source to be drawn toward the fluid pump by the negative pressure.

11. The method of claim 1, wherein the operation of the fluid pump is initiated such that the fluid is drawn from the arterial line set, through a dialyzer, through the venous line set, and into the patient.

12. The method of claim 1, wherein:
   the fluid in the arterial line set includes a first fluid, and
   the operation of the fluid pump is initiated while the access line is connected to a fluid source such that a second fluid is pumped from the fluid source through the arterial line set and the venous line set to convey the first fluid through the arterial line set and the venous line set into the patient.

13. The method of claim 12, wherein the first fluid includes blood.

14. The method of claim 12, wherein the second fluid includes saline.

15. The method of claim 1, wherein the fluid pump is driven in a direction in which the fluid pump is driven to perform an extracorporeal blood treatment on the patient.

16. The method of claim 1, wherein initiating the operation to generate the negative pressure comprises activating the fluid pump.

17. The method of claim 1, wherein initiating the operation to generate the negative pressure in the portion of the arterial line set comprises initiating the operation to generate the negative pressure in the portion of the arterial line set such that a signal generated by a sensor arranged to measure a value of pressure in the arterial line set is indicative of a negative value of pressure.

18. The method of claim 1, wherein initiating the operation to generate the negative pressure in the portion of the arterial line set comprises initiating the operation to generate the negative pressure in the portion of the arterial line set while a port of the arterial line set connectable to a fluid source is clamped.

19. The method of claim 1, wherein the access line comprises a first end connected to the arterial line set and a second end connectable to the arterial access, wherein clamping the access line comprises clamping a portion of the access line proximate the second end of the access line.

20. The method of claim 19, wherein the fluid comprises blood, and clamping the access line of the arterial line set comprises clamping the access line of the arterial line set to prevent the blood from flowing out of the access line through the second end of the access line.

21. An extracorporeal blood treatment system comprising:
a fluid pump configured to engage an arterial line set to convey fluid from a patient through the arterial line set, through a dialyzer, through a venous line set, and back to the patient during an extracorporeal blood treatment; and
a controller configured to operate the fluid pump to generate, while an access line of the arterial line set is clamped, negative pressure in a portion of the arterial line set between the fluid pump and the access line of the arterial line set such that the negative pressure generated in the portion of the arterial line while the access line of the arterial line set is clamped draws the fluid toward the fluid pump engaged to the arterial line set when the access line of the arterial line set is unclamped, and
infuse the fluid in the arterial line set into the patient through the venous line set while the access line of the arterial line set is unclamped.

22. The extracorporeal blood treatment system of claim 21, further comprising a pressure sensor to detect a value of pressure within the arterial line set, wherein the controller is configured to deactivate the fluid pump when the value of pressure exceeds a predefined value.

23. The extracorporeal blood treatment system of claim 21, further comprising an optical sensor to detect flow of blood through the venous line set, wherein the controller is configured to deactivate the fluid pump when the optical sensor detects an absence of the flow of blood through the venous line set.

24. The extracorporeal blood treatment system of claim 21, wherein the controller is configured to operate the fluid pump for a duration of time between 5 and 15 seconds, while the access line of the arterial line set is clamped, to generate the negative pressure.

25. The extracorporeal blood treatment system of claim 21, further comprising an ultrafiltration pump, wherein the controller is configured to deactivate the ultrafiltration pump and the fluid pump at an end of the extracorporeal blood treatment.

* * * * *

UNITED STATES PATENT AND TRADEMARK OFFICE
CERTIFICATE OF CORRECTION

PATENT NO. : 11,420,037 B2
APPLICATION NO. : 15/669287
DATED : August 23, 2022
INVENTOR(S) : Martin Joseph Crnkovich, David Yuds and Christian Schlaeper It is certified that error appears in the above-identified patent and that said Letters Patent is hereby corrected as shown below:

On the Title Page

Item (54) Column 1, Line 2, delete "EXTRACOPOREAL" and insert --EXTRACORPOREAL--.

In the Specification

Column 1, Line 2, delete "EXTRACOPOREAL" and insert --EXTRACORPOREAL--.

Signed and Sealed this
Twenty-second Day of November, 2022

Katherine Kelly Vidal
*Director of the United States Patent and Trademark Office*